United States Patent [19]

Fulmer et al.

[11] Patent Number: 4,626,600

[45] Date of Patent: Dec. 2, 1986

[54] PROCESS FOR PURIFYING ACETONE

[75] Inventors: John W. Fulmer, Mt. Vernon; William D. Kight, Poseyville, both of Ind.

[73] Assignee: General Electric Company, Mt. Vernon, Ind.

[21] Appl. No.: 703,990

[22] Filed: Feb. 21, 1985

Related U.S. Application Data

[63] Continuation-in-part of Ser. No. 609,322, May 11, 1984, abandoned.

[51] Int. Cl.$^4$ ............................................. C07C 45/80
[52] U.S. Cl. .................................... 568/411; 568/385; 568/798
[58] Field of Search ........................ 568/385, 411, 798

[56] References Cited

U.S. PATENT DOCUMENTS

| | | | |
|---|---|---|---|
| 2,734,085 | 2/1956 | Adams et al. | 568/385 |
| 2,737,480 | 3/1956 | Adams et al. | 568/385 |
| 2,904,592 | 9/1959 | Ellis et al. | 568/385 |
| 2,951,870 | 9/1960 | Cooke | 568/385 |
| 2,957,921 | 10/1960 | Adams | 568/385 |
| 3,215,745 | 11/1965 | Frank | 568/385 |
| 3,906,676 | 9/1959 | Beluley et al. | 568/385 |
| 4,434,305 | 2/1984 | Kurosaka et al. | 568/385 |

*Primary Examiner*—James H. Reamer
*Attorney, Agent, or Firm*—Martin B. Barancik

[57] ABSTRACT

In accordance with the invention there is a process for reducing the water content of acetone prepared from cumene which includes the steps of a. adding cleaving effective catalytic quantities of sulfuric acid to a mixture comprising cumene hydroperoxide and cumene, the cumene hydroperoxide making up about 81 to 83 weight percent of the said mixture, thereby producing a mixture comprising phenol, acetone, cumene and sulfuric acid;

b. neutralizing the said sulfuric acid with an aqueous alkali hydroxide and separating the alkali metal sulfate from the mixture comprising phenol, acetone, water and cumene, the water being from about 40 to 60 weight percent of the total weight of water and cumene, the cumene being present in sufficient quantities to cause the formation of two liquid phases upon condensing the acetone fraction distillate;

c. separating by distillation the acetone fraction from the phenol fraction, said acetone fraction containing acetone, water, aldehyde, and other organics including cumene;

d. condensing the said acetone fraction, the said acetone fraction separating into two phases, the bottom phase having a substantial portion of the water and aldehyde present in the said acetone fraction, the upper phase having a substantial portion of the cumene of the said acetone fraction, the acetone being partitioned between the bottom phase and the upper phase;

e. recycling at least a portion of the bottom phase to the vessel in which the sulfuric acid is neutralized and f. processing the upper phase to achieve a separation of the acetone and water.

3 Claims, 2 Drawing Figures

PROCESS FOR PURIFYING ACETONE

CROSS-REFERENCE TO RELATED APPLICATION

This application is a continuation-in-part of co-pending application Ser. No. 609,322, filed May 11, 1984 now abandoned.

BACKGROUND OF THE INVENTION

Phenol is a basic commodity chemical with many end uses. Most of the phenol manufactured is prepared from isopropylbenzene, hereafter referred to as cumene. The reaction sequence is short and entails the following steps:

1. Air oxidation of cumene to give cumene hydroperoxide.

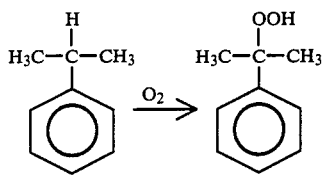

2. Acid cleavage of the hydroperoxide to provide phenol and acetone.

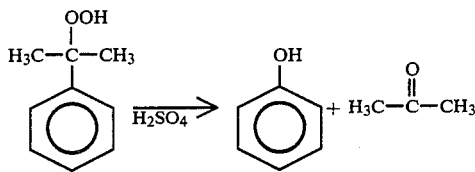

The phenol and acetone are separated and each one purified to the degree necessary to satisfy its ultimate use. As is readily observed, for every mole of phenol that is produced, a mole of acetone is also theoretically produced. Acetone is also a commodity chemical with various end uses. Although not shown in the schematic equations, there are by-products formed as well which must be removed to various degrees depending upon the end use of the phenol or acetone. Additionally other materials are introduced into the process to remove trace quantities of materials which may be deleterious to the products. One of these materials is water. It is usually introduced into the processing stream in the form of aqueous or slurried sodium hydroxide and is used to precipitate out the sulfate anion. As shown in the second equation above, the cleavage reaction is catalyzed by trace quantities of sulfuric acid. However, if the sulfuric acid remains in the processing stream, charring of products can occur. Therefore the sulfuric acid must be removed. This is usually done by contacting the reaction product of the cleavage reaction with aqueous or slurried sodium hydroxide in a vessel usually called a neutralizer. The sulfuric acid is neutralized and the sodium sulfate removed, usually as a dense aqueous solution. However, some of the water remains in the organic processing stream since it is soluble therein to a certain extent. Because of its relatively low boiling point it becomes associated with the low boiling acetone fraction distillate as opposed to the high boiling phenol fraction distillate. Under conventional acetone processing, the water is separated from the acetone in the final distillation tower as bottoms, the distillate acetone ready for sale in the market place. This final separation of water from acetone is very important since the product specification of commercial grade acetone should have no more than 0.5 wt. percent water. The less water in acetone, the higher is the quality of the product. Low water content acetone can command a higher price in the market place.

A new process for removing water from the acetone stream present in the sulfuric acid catalyzed cleavage of cumene hydroperoxide has been discovered. This process reduces the quantity of energy expended in separating acetone from water in the conventional processing. Furthermore, a final acetone purification column of substantially smaller size can now be employed. A product acetone with significantly reduced water content can be efficiently produced using the process of this invention.

DESCRIPTION OF THE INVENTION

In accordance with the invention there is a process for reducing the water content of acetone prepared from cumene which includes the steps of a. adding cleaving-effective catalytic quantities of sulfuric acid to a mixture comprising cumene hydroperoxide and cumene, the cumene hydroperoxide making up about 81 to 83 weight percent of the said mixture, thereby producing a mixture comprising phenol, acetone, cumene and sulfuric acid;

b. neutralizing the said sulfuric acid with an aqueous alkali hydroxide and separating the alkali metal sulfate from the mixture comprising phenol, acetone, water and cumene, the water being from about 40 to 60 weight percent of the total weight of water and cumene, the cumene being present in sufficient quantities to cause the formation of two liquid phases upon condensing the acetone fraction distillate in step d;

c. separating by distillation the overhead acetone fraction from the phenol fraction, said acetone fraction containing acetone, water, aldehyde, and other organics including cumene;

d. condensing the said acetone fraction, the said acetone fraction separating into two phases, the bottom aqueous phase having a substantial portion of the water and aldehyde present in the said acetone fraction, the upper organic phase having a substantial portion of the cumene of the said acetone fraction, the acetone being partitioned between the bottom phase and the upper phase;

e. recycling at least a portion of the bottom aqueous phase to the vessel in which the sulfuric acid is neutralized and f. processing the upper phase to achieve a separation of the acetone and water.

DETAILED DESCRIPTION OF THE INVENTION

Figure 1:
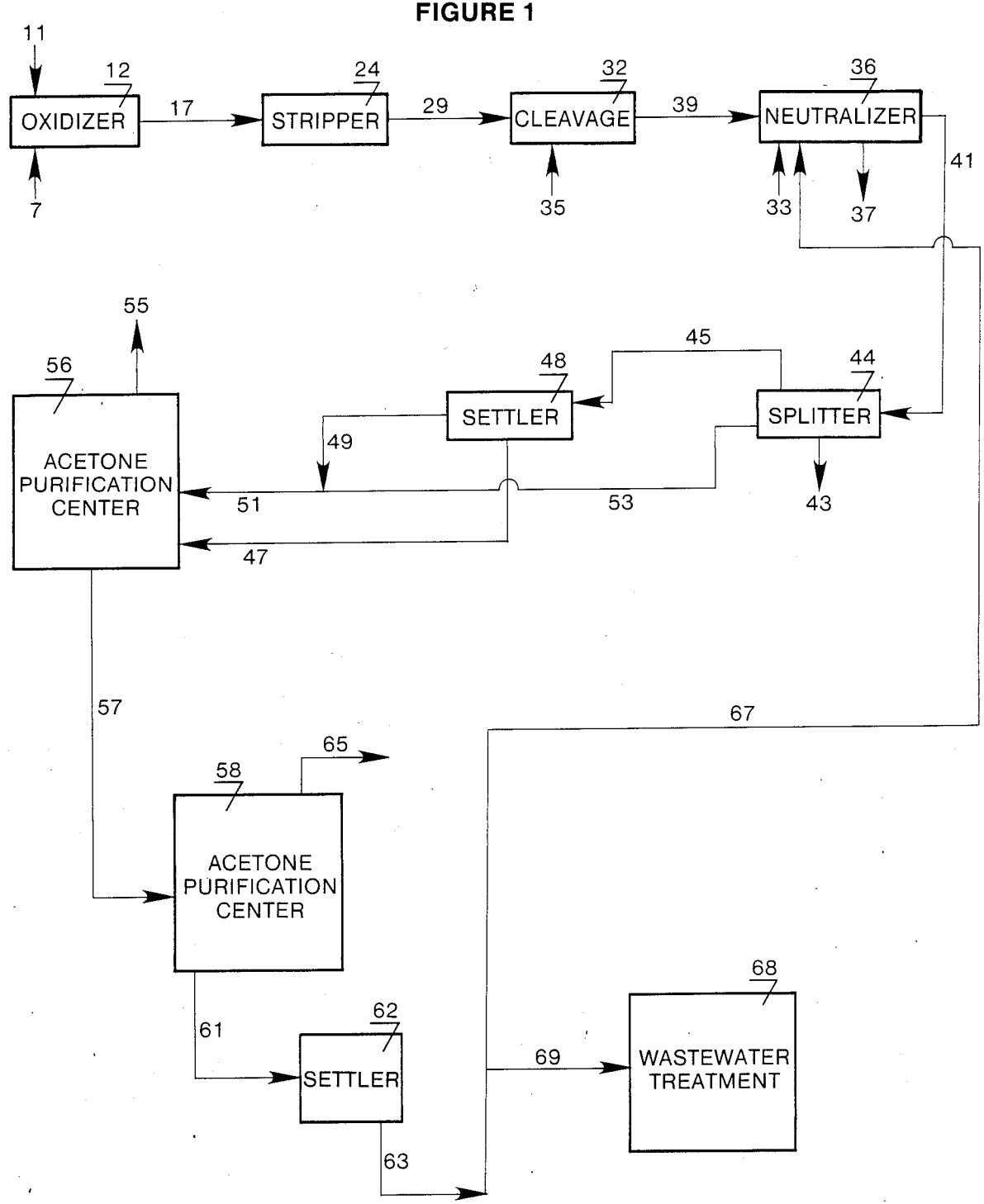

The conversion of cumene to phenol and acetone is a well known process utilizing individual process steps well known in the industry. The formation of the cumene hydroperoxide by the air oxidation of cumene is performed under standard conditions and the cumene hydroperoxide brought to a higher concentration by stripping substantial quantities of unreacted cumene. Generally the cumene hydroperoxide is about 81 to 83 weight percent of the feed fed to the cleavage area. The cumene present with the cumene hydroperoxide is generally at least about 10 parts by weight cumene to 100 parts by weight cumene hydroperoxide, preferably at least about 12 parts by weight, more preferably at least about 13 parts by weight. Generally no more than about 15 need be present. The cumene is needed to have the acetone condensate break into two layers. The easiest incorporation point for cumene in the processing train is to not separate the cumene completely from the cumene hydroperoxide. Other incorporation points can be in the cleavage area, neutralization area or the splitter itself. However at each of these points, cumene is being added back to a stream in which it was once present. Therefore it is preferred to leave with the cumene hydroperoxide the desired quantity of cumene.

To this concentrated quantity of cumene hydroperoxide is added a catalytic quantity of sulfuric acid which brings about the cleavage of cumene hydroperoxide to phenol and acetone. Generally from about 0.1 to 0.2 weight percent of the feed is sulfuric acid although this quantity can vary. Since the presence of even very small quantities of sulfuric acid can bring about charring in later processing step(s) it is important to remove the sulfuric acid. Conventionally used processing techniques treat the effluent phenol, acetone, side product and sulfuric acid with an aqueous alkali hydroxide, the alkali metal usually being sodium or potassium, preferably sodium. The alkali hydroxide is usually introduced into the neutralization vessel as a sodium hydroxide solution or slurry. The sulfuric acid is neutralized and sodium sulfate is formed. The concentration of water is maintained so that the sodium sulfate is continuously separated, preferably as a solution as opposed to a precipitate, as a lower phase from the organic phase of acetone, phenol and side products. However, some of the water is soluble in the organic phase. The weight of water to cumene entering the vessel wherein the acetone fraction is "split" from the phenol fraction is generally from about 40 to 60 weight percent water, as based upon water and cumene, preferably above 45 to 55 weight percent, most preferably about 50 to 50 weight percent.

The organic phase is then split, usually by distillation, into separate streams for further processing, the overhead acetone lower boiling stream and the bottom phenol higher boiling stream. Water is carried along with the acetone stream under conventional processing conditions until the final distillation wherein the water is finally separated from the acetone. This a difficult, time consuming separation and requires substantial energy and a relatively large multi-trayed column.

A portion of the water coming off as bottoms is recycled to the neutralizer area and is used to prepare the alkali hydroxide and/or maintain the water content in the neutralizer.

The process steps of this invention remove the water at an earlier time in the processing wherein the water is more concentrated and readily removable at this time. Thereby the acetone has a substantially decreased water content to be removed in the final distillation process.

The conventional process followed by the prior art will be explained in more detail following the flow chart of FIG. 1.

Figure 2:
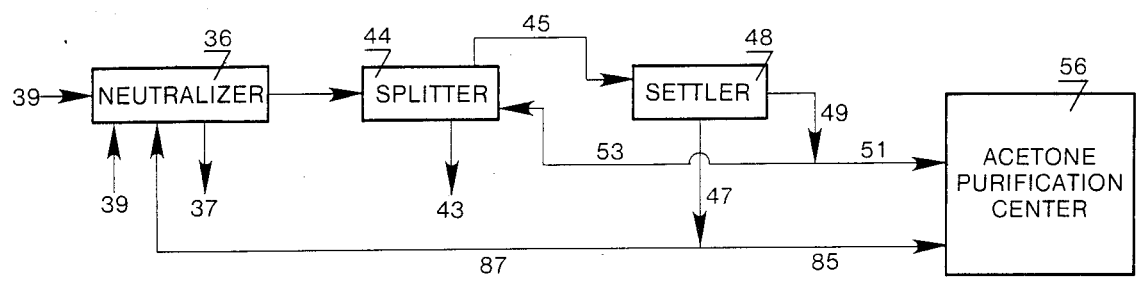

The flow chart of FIG. 2 illustrates the process of the invention.

Cumene enters oxidizer, 12, through line 11 and reacts with air brought in through line 7 to form cumene hydroperoxide. The cumene hydroperoxide is transported from the oxidizer through line 17 to the stripper, 24 wherein the cumene hydroperoxide is concentrated to a higher percent with the concomitant removal of substantial quantities of unreacted cumene. The concentrated cumene hydroperoxide and non removed cumene enters the cleavage reactor, 32 through line 29. A catalytic quantity of sulfuric acid is introduced into the cleavage reactor through line 35 and the cumene hydroperoxide cleaved into a mixture of phenol, acetone and by-products. The mixture is then transported to the neutralizer, 36, through line 39. Aqueous alkali hydroxide generally sodium hydroxide is introduced into neutralizer 36 through line 33. The aqueous alkali hydroxide neutralizes the sulfuric acid thereby forming alkali sulfate. The alkali sulfate is then removed from the neutralizer preferably as a dense aqueous solution, about 23 wt. percent alkali sulfate, through line 37. The phenol, acetone, solubilized water, cumene and reaction by-products are then transported through line 41 to the splitter, 44. In the splitter, the two major components, acetone and phenol, are separated usually by distillation. The phenol and heavier ends are removed as liquid through line 43 and are further processed. The acetone and other lighter end components, including water, aldehyde and other organics including cumene pass as overheads through line 45 to the settler, 48. The overheads condense and two phases separate. The bottom, denser phase has a substantial portion of the water and the aldehyde. The upper phase has a substantial portion of the cumene. The acetone is partitioned according to solubility between the two phases. The bottom aqueous phase is drawn off through line 47 to acetone purification center, 56. The upper hydrocarbon phase is removed from the settler through line 49 which is then separated into two lines, 51 and 53. Line 51 transports a portion of the upper phase to acetone purification center, 56. Line 53 transports the remainder of the upper phase to the splitter, 44, wherein it functions as a reflux oil maintaining the efficiency of the splitter. In acetone purification center, 56, aldehyde is separated from the acetone, water, cumene and organic material usually by distillation, the aldehydes leaving as overhead through line 55, the acetone, water, cumene and other organic material leaving as bottoms liquid through line 57. The bottoms are transported through line 57 to the final acetone purification center, 58, wherein acetone product is passed as overhead line 65, and the water, cumene and organic material are removed as bottoms in line 61. The water is separated from the cumene and organic material in the settler, 62, and the water withdrawn by line 63, which is split into two lines, 69 which goes to waste water treatment and the bulk of the water into line 67 which then recycles to the neutralizer, 36.

FIG. 2 shows the process of the invention. All the process steps are virtually the same. The changes occur in the transport of the bottom phase of the settler, 48, through line 47. Previously all of the bottom aqueous phase was transported to acetone treatment center, 56. In accordance with this invention, the contents of line 47 are split into two lines, 85 and 87. Line 87 carries a significant portion of the bottom phase of the settler back to the neutralizer, 36. In the neutralizer the water in line 87 can be properly employed to maintain the solution of the sodium sulfate and/or solubilize the alkali hydroxide. By a significant portion is meant that quantity which will reduce the quantity of water in product acetone a desireable amount. Obviously, this will vary according to the needs of the acetone producer. Generally, at least about 25 wt. percent of the bottom phase and preferably about 50 wt. percent or higher of the bottom phase can be recycled to the neutralizer, 36. All the water may be recycled to the neutralizer, 36, if desired. The remainder, if any is present, is transported to the acetone purification center by line 85, as previously done.

The results of this step are quite clear. A substantial portion of the water previously contaminating the acetone is no longer present in the acetone purification center. Rather this water is present in a closed loop between the neutralizer, 36, wherein the water can be efficiently employed and the settler, 48, wherein the water is substantially separated from the process stream.

This process is clearly advantageous in that there is less water contamination of acetone by water in the acetone product. The amount of energy necessary to perform the separation of acetone from water is substantially lessened. Still further, the size of the acetone water separation distillation column can be substantially reduced thereby decreasing the necessary capital investment. The process of this invention can reduce the water quantity in marketable acetone to less than or equal to about 0.1 weight percent.

The examples below are intended to illustrate the invention and not limit it.

Two plant tests were performed wherein 50% and 75% of the #48 settler aqueous phase volume flow rate was directed to the neutralizer, 36, and not allowed to feed forward to the acetone purification center. The cumene hydroperoxide was 82 weight percent of the feed to the cleavage area. The cumene present in the feed was 13 parts by weight per 100 parts of the cumene. The water to cumene ratio entering the splitter from the neutralizer is about 1:1 on a weight basis.

| #48 SETTLER AQUEOUS FLOW RATE TO NEUTRALIZER, 36 | #65 PROCUCT ACETONE WT. % H$_2$O |
|---|---|
| 0 (Prior Art) | 0.28 |
| 50% | 0.16 |
| 75% | 0.09 |

The data in the Table is clear. When prior art practices are being followed, the weight percent water in the acetone is 0.28. When 50 weight percent of the bottom aqueous phase volume is recycled to the neutralizer, rather than feed through the acetone distillation train, a 43% reduction in water contamination of acetone, is achieved. When 75 weight percent of the bottom aqueous phase volume is recycled to the neutralizer, a 66% reduction of water contamination of acetone is achieved.

What is claimed is:

1. A process for reducing the water content of acetone prepared from cumene which includes the comprises
   a. adding cleaving-effective catalytic quantities of sulfuric acid to a mixture comprising cumene hydroperoxide and cumene, the cumene hydroperoxide making up about 81 to 83 weight percent of the said mixture and the cumene at least 10 parts by weight as measured by 100 parts by weight cumene hydroperoxide, thereby producing a mixture comprising phenol, acetone, cumene and sulfuric acid;
   b. neutralizing the said sulfuric acid with an aqueous alkali hydroxide and separating the alkali metal sulfate from the mixture comprising phenol, acetone, water and cumene, the water being from about 40 to 60 weight percent of the total weight of water and cumene, the cumene being present in sufficient quantities to cause the formation of two liquid phases upon condensing the acetone fraction distillate in step d;
   c. separating by distillation the overhead acetone fraction from the phenol fraction, said acetone fraction containing acetone, water, aldehyde, and other organics including cumene;
   d. condensing the said acetone fraction, the said acetone fraction separating into two phases, the bottom aqueous phase having a substantial portion of the water and aldehyde present in the said acetone fraction, the upper organic phase having a substantial portion of the cumene of the said acetone fraction, the acetone being partitioned between the bottom phase and the upper phase;
   e. recycling at least a portion of the bottom aqueous phase to the vessel in which the sulfuric acid is neutralized and
   f. processing the upper phase to achieve a separation of the acetone and water.

2. A process in accordance with claim 1 wherein at least about 25 wt. percent of the bottom phase is recycled.

3. A process in accordance with claim 2 wherein at least about 50 wt. percent of the bottom phase is recycled.

* * * * *